United States Patent [19]
Galante

[11] Patent Number: 5,502,191
[45] Date of Patent: Mar. 26, 1996

[54] METHOD OF SYNTHESIZING STERICALLY HINDERED 5-SUBSTITUTED-1H-TETRAZOLES FROM NITRILES USING A LEWIS ACID AND AN AZIDE

[75] Inventor: Rocco J. Galante, Somerville, N.J.

[73] Assignee: American Cyanamid Company, Madison, N.J.

[21] Appl. No.: 391,317

[22] Filed: Feb. 17, 1995

Related U.S. Application Data

[63] Continuation of Ser. No. 87,626, Jul. 1, 1993, abandoned.
[51] Int. Cl.⁶ .................................................. C07D 239/90
[52] U.S. Cl. ..................... 544/284; 544/287; 544/290; 548/250; 548/252; 548/254
[58] Field of Search .................................. 544/284, 287, 544/290; 548/250, 252, 254

[56] References Cited

PUBLICATIONS

Advance Organic Chemistry, Jerry March, pp. 227–229, 1985.
Finnegan et al. J. Am. Chem. Soc., 80 pp. 3908–3911, 1958.

*Primary Examiner*—Yogendra N. Gupta
*Attorney, Agent, or Firm*—Arthur G. Seifert

[57] ABSTRACT

A method for making 5-substituted tetrazoles of formula I:

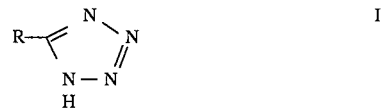

where R is as herein described which comprises reacting a compound of the formula R—CN with a Lewis acid and an azide or a preformed metal azide complex, acidifying and recovering the 5-substituted tetrazole.

2 Claims, No Drawings

METHOD OF SYNTHESIZING STERICALLY HINDERED 5-SUBSTITUTED-1H-TETRAZOLES FROM NITRILES USING A LEWIS ACID AND AN AZIDE

This is a continuation of co-pending application Ser. No. 08/087,626 filed on Jul. 1, 1993.

BACKGROUND OF THE INVENTION

The invention is a process for making 5-substituted-1H-tetrazoles from nitriles using a Lewis acid and an azide or a preformed metal azide complex. The process is exceptionally useful for synthesizing sterically hindered 5-substituted-1H-tetrazoles.

The classical method (W. G. Finnegan et al., *J. Am. Chem. Soc.* 1958, 80, 3908) of synthesizing tetrazoles from nitriles uses ammonium chloride/sodium azide/N,N-dimethylformamide, but this fails to react, in acceptable yield and purity, on sterically hindered nitriles. Hindered 5-substituted-1H-tetrazoles cannot be synthesized in acceptable yield or purity using ammonium chloride/sodium azide/N,N-dimethylformamide. Exothermic decomposition of the reaction products occurs yielding volatile products with a large heat of decomposition, thereby making the reaction unsafe.

The method of J. V. Duncia (*J. Org. Chem.*, 1991, 56, 2395) uses trimethyltin or tributyltin azide to produce tetrazoles in good yield. Trimethyltin azide must be prepared in advance and tributyltin azide is prepared in situ. When working with large scale preparations, the tin by-products are difficult to remove, thus requiring extensive and tedious chromatography. The use of anhydrous hydrogen chloride gas, used to cleave the tin-tetrazole bond, is not desired when working with large quantities.

The sterically hindered 5-substituted tetrazoles of the present invention are useful as intermediates in a variety of compounds, particularly as intermedaites in preparing biphenyl-tetrazole angiotensin II receptor antagonists useful as cardiovascular agents. See, for example European Patent Application No. EP-253310, EP-324377, and EP-497150.

SUMMARY OF THE INVENTION

The invention is a process for synthesizing 5-substituted tetrazoles of formula I:

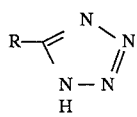

I wherein

R is selected from: (a) straight or branched, substituted or unsubstituted ($C_1$–$C_6$)alkyl, wherein the substitution is hydrogen, ($C_1$–$C_6$)alkyl, ($C_1$–$C_6$)alkoxy, hydroxyl, nitro, trifluoromethyl, pyridine, thiophene, furan, phenyl, or substituted phenyl wherein the substitution is ($C_1$–$C_3$)alkyl, trifluoromethyl, nitro, —O($C_1$–$C_3$)alkyl, or amino; and (b) moieties of the formula:

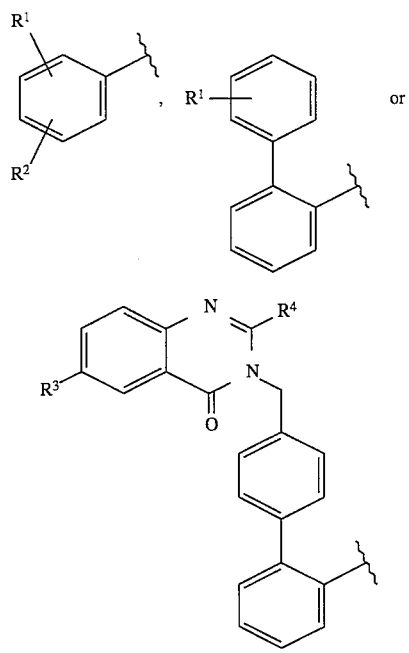

$R^1$ and $R^2$ are independently selected from hydrogen, halogen, ($C_1$–$C_6$)alkyl, ($C_1$–$C_6$)alkoxy, hydroxyl, nitro, trifluoromethyl, pyridine, thiophene, furan, phenyl and substituted phenyl wherein the substitution is ($C_1$–$C_3$)alkyl, trifluoromethyl, nitro, —O($C_1$–$C_3$)alkyl, or amino;

$R^3$ is a substituted or unsubstituted, straight or branched ($C_1$–$C_9$)alkyl wherein the substitution is hydrogen, ($C_1$–$C_4$)alkyl, phenyl, substituted phenyl wherein the substitution is ($C_1$–$C_3$)alkyl, trifluoromethyl, nitro, —O($C_1$–$C_3$)alkyl, or amino; pyridine, thiophene, furan, —O($C_1$–$C_4$)alkyl, hydroxyl or ($C_1$–$C_4$)alkyl—C(=O)—O—;

$R^4$ is ($C_1$–$C_6$)alkyl;

and the pharmaceutically acceptable salts thereof; which comprises:

reacting a compound of formula: R—CN wherein R is as defined hereinabove; with a Lewis acid and an azide or a preformed metal azide complex, in a polar solvent at reflux temperature for from 4 to 72 hours; acidifying and recovering the 5-substituted tetrazole I so produced in excellent yield and purity.

The preferred compounds of formula I are those wherein:

R is selected from (a) straight or branched, substituted or unsubstituted ($C_1$–$C_6$)alkyl, wherein the substitution is hydrogen, ($C_1$–$C_6$)alkyl, ($C_1$–$C_6$)alkoxy, hydroxyl, nitro, trifluoromethyl, pyridine, thiophene, furan, phenyl, or substituted phenyl wherein the substitution is ($C_1$–$C_3$)alkyl, trifluoromethyl, nitro, —O($C_1$–$C_3$)alkyl, or amino; and (b) moieties of the formulae:

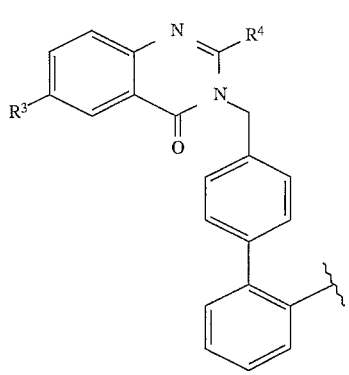 or 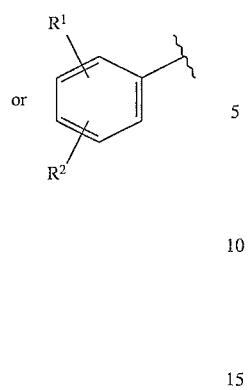

R$^1$ and R$^2$ are independently selected from hydrogen, halogen, (C$_1$-C$_6$)alkyl, (C$_1$-C$_6$)alkoxy, hydroxyl, nitro, trifluoromethyl, pyridine, thiophene, furan, phenyl and substituted phenyl wherein the substitution is (C$_1$-C$_3$)alkyl, trifluoromethyl, nitro, —O(C$_1$-C$_3$)alkyl, or amino;

R$^3$ is selected from moieties of the formulae:

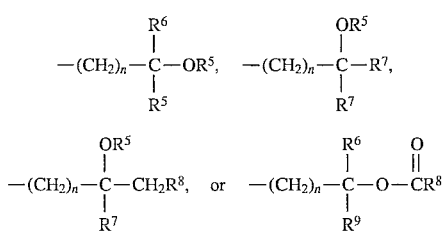

wherein

R$^5$ is hydrogen or (C$_1$-C$_4$)alkyl;

R$^6$ is hydrogen, (C$_1$-C$_4$)alkyl, pyridine, thiophene, furan, phenyl, or substituted phenyl wherein the substitution is (C$_1$-C$_3$)alkyl, trifluoromethyl, nitro, —O(C$_1$-C$_3$)alkyl, or amino;

R$^7$ is (C$_1$-C$_4$)alkyl, pyridine, thiophene, furan, phenyl, or substituted phenyl wherein the substitution is (C$_1$-C$_3$)alkyl, trifluoromethyl, nitro, —O(C$_1$-C$_3$)alkyl, or amino;

R$^8$ is (C$_1$-C$_4$)alkyl;

R$^9$ is hydrogen, (C$_1$-C$_4$)alkyl, pyridine, thiophene, furan, phenyl, or substituted phenyl wherein the substitution is (C$_1$-C$_3$)alkyl, trifluoromethyl, nitro, —O(C$_1$-C$_3$)alkyl, or amino;

R$^4$ is (C$_1$-C$_6$)alkyl;

n is an integer from 0–3;

and the pharmaceutically acceptable salts thereof.

The most preferred compounds of formula I are those wherein:

R is selected from (a) substituted (C$_1$-C$_6$)alkyl wherein the substitution is hydrogen, (C$_1$-C$_6$)alkyl, (C$_1$-C$_6$)alkoxy, hydroxyl, nitro, trifluoromethyl, pyridine, thiophene, furan, phenyl, or substituted phenyl wherein the substitution is (C$_1$-C$_3$)alkyl, trifluoromethyl, nitro, —O(C$_1$-C$_3$)alkyl, or amino; and (b) moieties of the formulae:

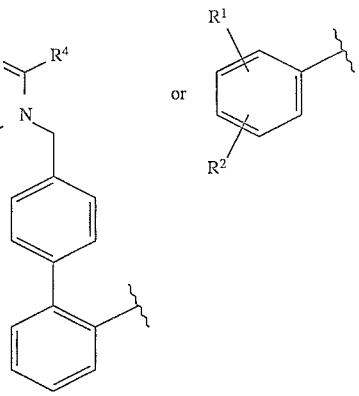

R$^1$ and R$^2$ are independently selected from hydrogen, halogen, (C$_1$-C$_6$)alkyl, (C$_1$-C$_6$)alkoxy, hydroxyl, nitro, trifluoromethyl, pyridine, thiophene, furan, phenyl, or substituted phenyl wherein the substitution is (C$_1$-C$_3$)alkyl, trifluoromethyl, nitro, —O(C$_1$-C$_3$)alkyl, or amino;

R$^3$ is selected from moieties of the formulae:

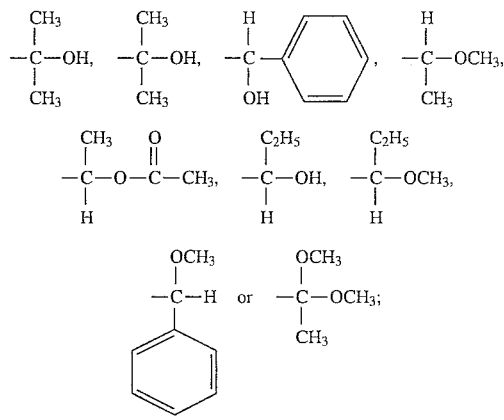

R$^4$ is (C$_3$-C$_4$)alkyl; and the pharmaceutically acceptable salts thereof.

The most particularly preferred compounds of formula I are those wherein:

R is selected from substituted (C$_1$-C$_6$)alkyl wherein the substitution is hydrogen, (C$_1$-C$_6$)alkyl, (C$_1$-C$_6$)alkoxy, hydroxyl, nitro, trifluoromethyl, pyridine, thiophene, furan, phenyl, or substituted phenyl wherein the substitution is (C$_1$-C$_3$)alkyl, trifluoromethyl, nitro, —O(C$_1$-C$_3$)alkyl, or amino; and moieties of the formula:

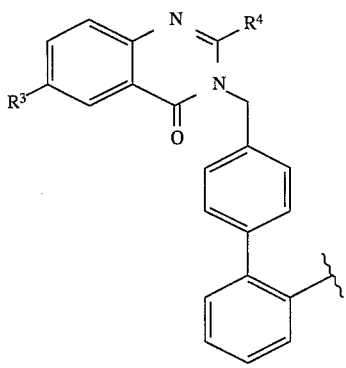

R³ is selected from moieties of the formulae:

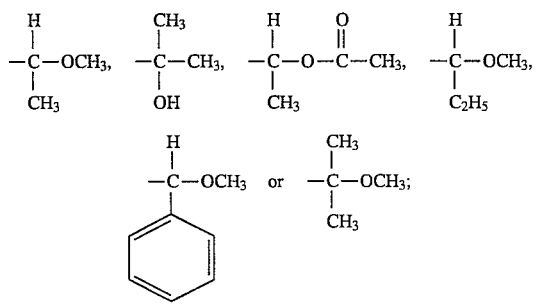

R⁴ is (C₄)alkyl; and the pharmaceutically acceptable salts thereof.

The Lewis acid is any acceptable Lewis acid as known in the art such as zinc chloride, magnesium chloride, aluminum chloride, aluminum isopropoxide or tin tetrachloride. The azide is sodium azide or trimethylsilyl azide and equivalents thereof. A preformed metal azide complex, zinc azide bispyridine complex, may be used instead of the separate Lewis acid and azide.

In the present invention the temperature of the reaction is able to go higher without decomposing the reagent. The higher reaction temperature makes it possible to react very hindered nitriles, such as 2,2-dimethylbenzylnitrile and 2,2-diphenylpropionitrile, with a Lewis acid and an azide or the preformed metal azide complex, to obtain the corresponding 5-substituted-1H-tetrazole.

The above conditions have not been used previously in the synthesis of 5-substituted-1H-tetrazoles.

The advantages of using the procedure of this invention are:

1. the reagent does not have to be prepared in advance;
2. the yields are higher overall;
3. the work-up procedure is simple;
4. the products are purer and do not need to be chromatographed before they are used;
5. the reaction times are shorter;
6. the reagents are cheaper;
7. the reagents are less toxic and there is no odor problem; and
8. hindered 5-substituted-1H-tetrazoles can be synthesized in high yield.

DETAILED DESCRIPTION OF THE INVENTION

The process and compounds of the present invention are described in the following reaction:

SCHEME 1

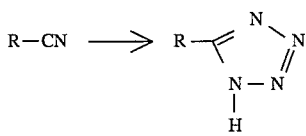

In accordance with Scheme 1, 1 mole of R—CN, wherein R is as defined hereinabove, dissolved in a polar solvent is preferably reacted with 3 moles of a Lewis acid and 5.05 moles of an azide for from 4–72 hours at the reflux temperature of the reaction. The reaction is cooled to room temperature and acidified to pH 1 with 10% aqueous hydrochloric acid. The acidified solution is added to ice water, stirred and the resulting precipitate is collected. The solid is washed with water and dried. The purity of the products is such that no further purification (chromatography or recrystallization) is required.

Preferably, the process is carried out such that the molar ratio of reactants is 1 mole of nitrile:3 moles of Lewis acid:5.05 moles of sodium azide (1:3:5.05).

As stated, the process of the present invention provides a method of preparing the hindered tetrazoles in significantly higher yields than the procedures of the prior art. For example, J. V. Duncia (*J. Org. Chem.*, 1991, 56, 2395) prepares the hindered 5-[1,1-diphenylethyl]-1H-tetrazole, in 9% yield. In contrast thereto, using the method of the present invention, we are able to prepare 5-[1,1-diphenylethyl]-1H-tetrazole in 87% yield.

The following specific examples are provided to further illustrate the process of the present invention and the manner in which it may be carried out. It will be understood, however, that the specific details given in the examples have been chosen for purposes of illustration and are not to be construed as a limitation on the invention.

EXAMPLE 1

5-(4'-Methyl[1,1'-biphenyl]-2-yl)-1H-tetrazole

To a 700 g solution of 4'-methyl[1,1'-biphenyl]-2-carbonitrile in 10 liters of N,N-dimethylformamide, is added 1438 g of zinc chloride and 1180 g of sodium azide. The reaction mixture is heated at reflux temperature for 36 hours, cooled to room temperature and acidified with 9.8 liters of 10% aqueous hydrochloric acid(pH 1). The resulting solution is added with stirring to 48 liters of ice-water and the mixture is stirred for one hour. The precipitate is collected, washed with water, and dried in a forced air oven at 50° C. to give 807 g (yield=94% of theory) of the desired product.

mp 144°–148° C.

Purity=92.7 area % by HPLC

EXAMPLE 2

5-(4'-Methyl[1,1'-biphenyl]-2-yl)-1H-tetrazole

The title compound is prepared by the procedure of Example 1 using 1.49 g of 4'-methyl[1,1'-biphenyl]-2-carbonitrile, 10 ml of N,N-dimethylformamide, 4.47 g of zinc azide bis-pyridine complex (P. Rollin et al., *Synthesis*, 1990, 130), heated at reflux temperature for 18.25 hours, to give 1.6 g (yield= 89% of theory) of the desired product.

mp 148°–149.5° C.

Purity=99.3 area % by HPLC.

EXAMPLE 3

5-(4'-Methyl[1,1'-biphenyl]-2-yl)-1H-tetrazole

The title compound is prepared by the procedure of Example 1 using 2.0 g of 4'-methyl[1,1'-biphenyl]-2-carbonitrile, 30 ml of N,N-dimethylformamide, 2.96 g of magnesium chloride and 3.37 g of sodium azide, heated at reflux temperature for 54 hours, to give 2.1 g (yield=84% of theory) of the desired product.

mp 144°–148° C.

Purity=96.0 area % by HPLC.

Substantially following the methods described in detail hereinabove, the compounds of this invention listed below in Examples 4–6 and 9–11 are prepared.

EXAMPLE 4

5-Phenyltetrazole

| | |
|---|---|
| Starting Material | benzonitrile |
| Reagent | zinc chloride and sodium azide |
| Solvent | N,N-dimethylformamide |
| Reaction Time | 4 hours |
| % Yield | 83 |
| mp | 216.6–217.9° C. |

EXAMPLE 5

5-(2-Bromophenyl)-1H-tetrazole

| | |
|---|---|
| Starting Material | 2-bromobenzonitrile |
| Reagent | zinc chloride and sodium azide |
| Solvent | N,N-dimethylformamide |
| Reaction Time | 21 hours |
| % Yield | 51 |
| mp | 181–184° C. |
| IR(cm$^{-1}$) | 1605, 1248, 1057, 1029, 749 |

EXAMPLE 6

5-(2,5-dimethylphenyl)-1H-tetrazole

| | |
|---|---|
| Starting Material | 2,5-dimethylbenzonitrile |
| Reagent | zinc and sodium azide |
| Solvent | N,N-dimethylformamide |
| Reaction Time | 4.5 hours |
| % Yield | 61 (due to impure starting material) |
| mp | 157–162° C. |
| IR(cm$^{-1}$) | 1587, 1507, 1250, 1059, 1040, 815 |
| $^1$H NMR(d$_6$-DMSO)d | 7.52(s,1H), 7.40–7.29(m,2H); 2.44(s,3H); 2.35(s,3H). |

EXAMPLE 7

5-(2-Methoxyphenyl)-1H-tetrazole

The title compound is prepared by the procedure of Example 1 using 2-methoxybenzonitrile, zinc chloride, sodium azide and N,N-dimethylformamide. The reaction is heated at reflux temperature for 5 hours, acidified with 10% hydrochloric acid, extracted with ethyl acetate, dried and concentrated in vacuo. The residue is chromatographed (silica gel: 50% ethyl acetate/methylene chloride) to give 2.57 g (yield=36% of theory).

| | |
|---|---|
| mp | 134–140° C. |
| IR(cm$^{-1}$) | 1610, 1484, 1253, 1070, 1016, 748 |

EXAMPLE 8

2-Butyl-6-(1-methoxy-1-methylethyl)-3-[[2'-(1H-tetrazol-5-yl)[1,1'-biphenyl]-4-yl]methyl-4(3H)-quinazolinone To a solution of 2.04 g of 4'-[[2-butyl-6-(1-methoxy-1-methylethyl)-4-oxo-3 (4H)-quinazolinyl]methyl]-[1,1'-biphenyl]-2-carbonitrile, prepared by the procedure described in B-765, in 40 ml of N,N-dimethylformamide is added 1.2 g of zinc chloride and 1.14 g of sodium azide. The reaction is heated at reflux temperature for 24.5 hours. An additional 1.2 g of zinc chloride and 1.14 g of sodium azide is added and the reaction is heated at reflux temperature for an additional 24.5 hours. The reaction is again recharged with 0.6 g of zinc chloride and 0.57 g of sodium azide and the heating continued for 18.5 hours. The mixture is cooled to room temperature and acidified to pH 1 with 50 ml of 10% hydrochloric acid. The mixture is added with stirring to 150 ml of ice-water and stirred for 1 hour. The resulting precipitate is collected, washed with water and dried in vacuo at 50° C. to give 1.6 g of the desired product.

Purity=87.6 area % by HPLC is desired product; 4.7 area % is starting material.

$^1$H NMR(CDCl$_3$): d 8.24(s, 1H); 8.0–7.75(m, 3H); 7.55–7.26 (m, 3H); 7.13–7.12(m, 4H); 5.43(br s, 2H); 3.11–3.08 (m, 2H); 3.07(s, 3H); 1.85–1.70(m, 2H); 1.55(s, 6H); 1.55–1.38(m, 2H); 0.88(t, 3H, J=7.3 Hz).

EXAMPLE 9

2-(1H-Tetrazol-5-yl)phenol

| | |
|---|---|
| Starting Material | 2-cyanophenol |
| Reagent | zinc chloride and sodium azide |
| Solvent | N,N-dimethylformamide |
| Reaction Time | 4 hours |
| % Yield | 76 |
| mp | 225–227° C. |
| IR(cm$^{-1}$) | 3200, 1618, 1509, 1363, 1245, 1216, 1067, 1016, 748 |

EXAMPLE 10

5-(1-Methyl-1-phenylethyl)-1H-tetrazole

| | |
|---|---|
| Starting material | 2,2-dimethylbenzylnitrile |
| Reagent | zinc chloride and sodium azide |
| Solvent | N,N-dimethylformamide |
| Reaction Time | 18 hours |
| % Yield | 75 |
| mp | 148–150° C. |
| IR(cm$^{-1}$) | 1494, 1262, 1041, 751, 703 |
| $^1$H NMR(CDCl$_3$)d | 7.34–7.16(m,5H); 1,84(s,6H) |

EXAMPLE 11

5-[1,1-Diphenylethyl]-1H-tetrazole

| | |
|---|---|
| Starting Material | 2,2-diphenylpropionitrile |
| Reagent | zinc chloride and sodium azide |
| Solvent | N,N-dimethylformamide |
| Reaction Time | 51.5 hours |
| % Yield | 87 |

-continued

| mp | 130–134° C. |
|---|---|
| IR(cm$^{-1}$) | 1595, 1494, 1268, 1067, 1029, 756, 700 |
| $^1$H NMR(CDCl$_3$)d | 7.40–7.20(m,6H); 7.20–7.00(m,4H): 2.19(s,3H); |

We claim:

1. A process for making 5-substituted tetrazoles of formula I:

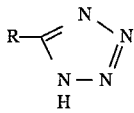

wherein

R is selected from moieties of the formulae:

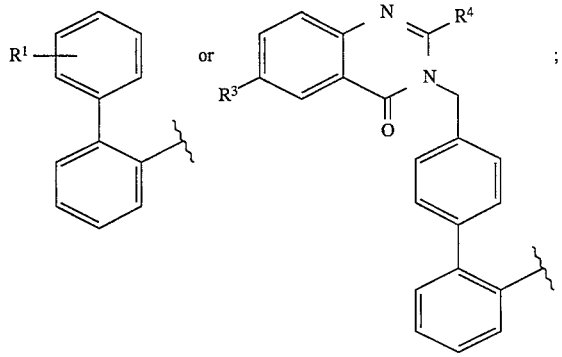

wherein $R^1$ is selected from hydrogen, halogen, $(C_1-C_6)$alkyl, $(C_1-C_6)$alkoxy, hydroxyl, phenyl and substituted phenyl wherein the substitution is selected from $(C_1-C_3)$alkyl, and $-O(C_1-C_3)$-alkyl;

$R^3$ is selected from

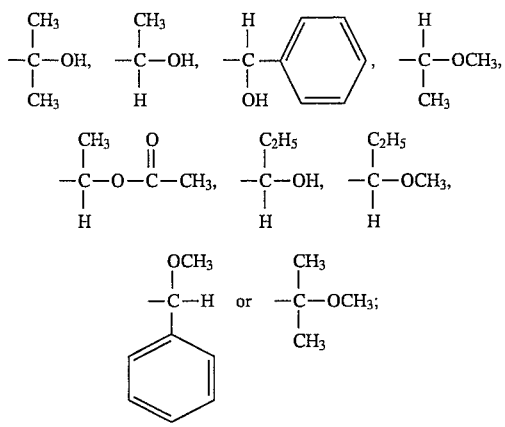

$R^4$ is $(C_3-C_4)$alkyl; which comprises:
reacting a compound of formula: R—CN wherein R is as defined hereinabove; with a zinc azide bispyridine preformed metal azide complex, in a polar solvent at reflux temperature for from 4 to 72 hours; acidifying and recovering the 5-substituted tetrazole I so produced.

2. The process of claim 1, wherein 5-(4'-methyl[1,1'-biphenyl]-2-yl)-1H-tetrazole is produced.

* * * * *